United States Patent [19]
Robioneck et al.

[11] Patent Number: 6,106,557
[45] Date of Patent: Aug. 22, 2000

[54] RECONSTRUCTION SYSTEM FOR VERTEBRA

[75] Inventors: Bernd Robioneck, Preetz, Germany; Richard G. Vlasak, Gainesville, Fla.; Rainer Kotz; Reinhard Windhager, both of Vienna, Austria; Paul Wuisman, Amsterdam, Netherlands

[73] Assignee: Howmedica GmbH, Germany

[21] Appl. No.: 09/359,271

[22] Filed: Jul. 22, 1999

[30] Foreign Application Priority Data

Jul. 23, 1998 [DE] Germany ............ 298 13 139 U

[51] Int. Cl.⁷ .................................................. A61F 2/44
[52] U.S. Cl. ............................ 623/17; 606/60; 606/61
[58] Field of Search ........................... 623/11, 16, 17, 623/20, 21; 606/60, 61

[56] References Cited

U.S. PATENT DOCUMENTS

| | | | |
|---|---|---|---|
| 5,002,576 | 3/1991 | Fuhrmann et al. | 623/17 |
| 5,192,327 | 3/1993 | Brantigan | 623/17 |
| 5,397,364 | 3/1995 | Kozak et al. | 623/17 |
| 5,522,899 | 6/1996 | Michelson | 623/17 |

*Primary Examiner*—Gene Mancene
*Assistant Examiner*—Pedro Philogene
*Attorney, Agent, or Firm*—Lerner, David, Littenberg, Krumholz & Mentlik, LLP

[57] ABSTRACT

A reconstruction system for vertebra, with at least one annular middle body and two annular end bodies. The end surfaces of the middle body and of the end bodies are formed such that the bodies may be stacked over one another and one end surface of the end bodies comprises a receiving section. The system includes two approximately right-angled vertebra body plates having a pair of limbs. One limb is formed such that in a direction perpendicular to the axis of an end body, it is insertable into the receiving section in a manner such that the one limb is prevented from moving away from the end body in the direction of the axis. The other limb comprises at least one bore for a bone screw and at least one threaded bore. A connection plate is provided, which at the ends comprises openings for connection to the other limb of each vertebra body plate via a screw.

20 Claims, 6 Drawing Sheets

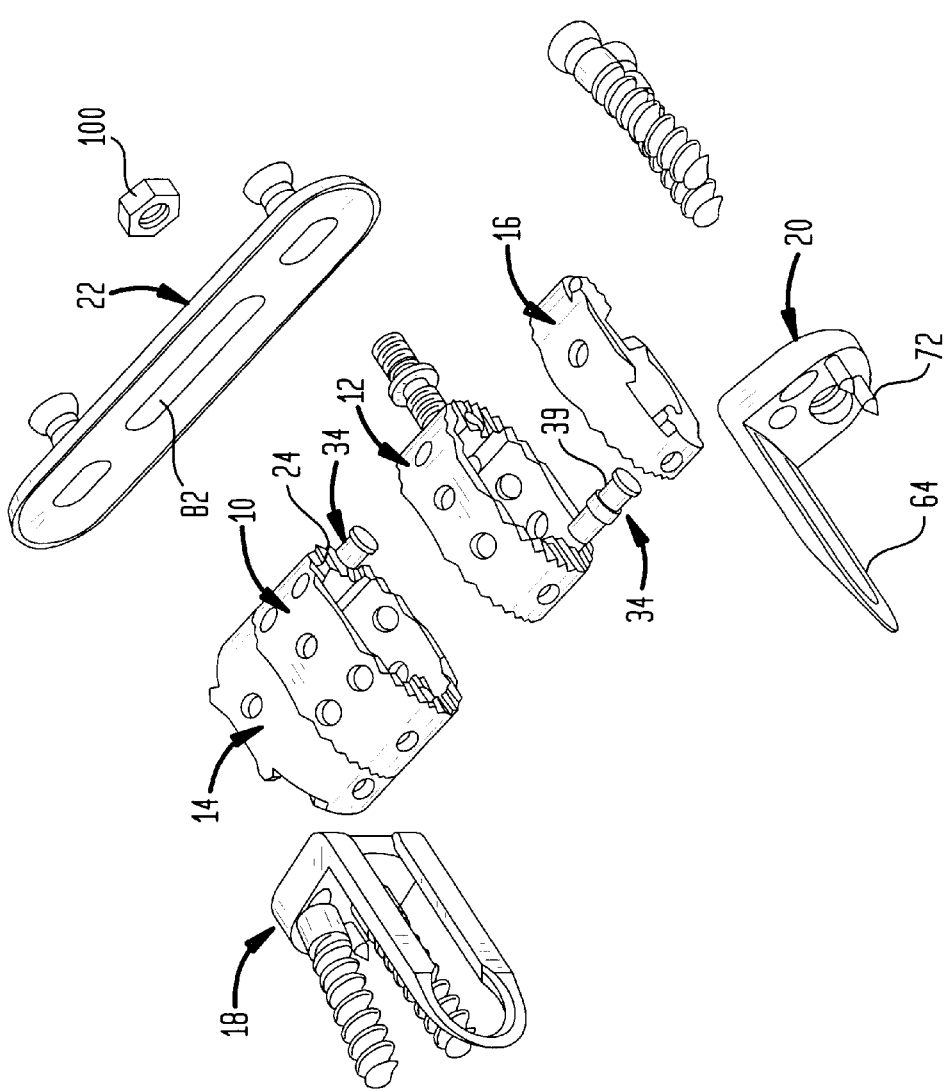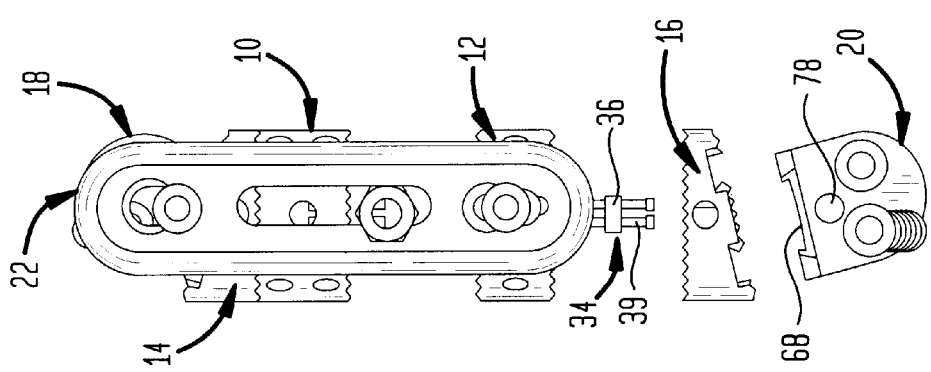

RECONSTRUCTION SYSTEM FOR VERTEBRA

BACKGROUND OF THE INVENTION

1. Field of the Invention

The invention relates to a reconstruction system for vertebra.

2. Description of Prior Art

With the removal of a part of a vertebra or vertebra body of the human vertebral column a replacement is provided which fills in the remaining space and assumes a carrying or support function. In this context a range of various implants are known. The implants are often cage-like and on the bearing surfaces are provided with teeth or the like in order to simplify a fastening of the neighboring vertebra bodies as well as an ingrowing of the bone tissue. It is also known to provide a set of such vertebra body space retainers which have a graded height. It is further known to telescopically arrange ring-like vertebra body space retainers and to mutually fasten them via screw connections. In this manner in steps the height of the whole arrangement may be adjusted.

SUMMARY OF THE INVENTION

It is an object of the invention to provide a reconstruction system for vertebra which is modularly constructed for adaptation to the respective circumstances of a human vertebral column and which in particular makes possible a stable variable reconstruction.

The reconstruction system according to the invention comprises one or more middle bodies as well as two annular end bodies. The annular middle body may be provided in graded lengths. The end bodies are preferably of a predetermined height, and otherwise may be designed the same. The end and the middle bodies may be stacked onto one another and comprise correspondingly adapted bearing surfaces. Furthermore it is essential to the invention that approximately right angled vertebra body plates are provided, each plate having a pair of limbs. One limb of the plates is formed such that it cooperates with a receiving section of an end body. For this purpose the corresponding limb of the plate extending transversely to the axis of the end body is inserted into the receiving section so that it is prevented from a movement in the axial direction away from the end body when the vertebra plate for its part is arranged rigidly i.e. attached to bone. For this purpose the other limb comprises at least one bore for leading through a bone screw. It faces away from the end body when the other limb is inserted into the end body. The plate may therefore be fastened in the neighboring vertebra or vertebra body in an angularly stable manner with the help of the bone screw. Since both end bodies are connected via a retaining plate to "healthy vertebra" the "column" or the "stack" of the bodies are securely anchored in the vertebral column.

So that however a further stability is obtained, a connection plate is provided which by way of a screw connection is connected to the outer lying limbs of the vertebra body plates.

According to one embodiment of the invention it is envisaged for the bodies to be formed ovally and the axis of the receiving section to run along the larger axis of the oval. The oval shape serves the adaptation to the corresponding shape of the vertebra body. The bone screws for fastening the vertebra body plate are positioned to laterally penetrate into the vertebra body of the healthy vertebra and a penetration into the vertebra hole is prevented.

According to a further embodiment of the invention it is envisaged for the cooperating end surfaces of the bodies to comprise teeth arranged in a manner such that the bodies are displaceable to one another only in one direction. The displacement direction runs preferably in the direction of the large axis of the oval. By way of this teeth arrangement, the stacking of the bodies during installation or implantation is simplified and a securement for a displacement against one another is obtained. A securement against a displacement in the direction of the tooth apexes or roots is prevented by the connection plate.

The end surfaces of the middle body are preferably formed the same. It is therefore immaterial which of the bearing surfaces of the middle body face upwards or downwards. The end surfaces of the end bodies, which face the middle body, are preferably formed complementarily to the end surfaces of the middle body.

Various possibilities for forming the receiving section in the end body are conceivable. One embodiment of the invention provides for the receiving section to comprise a dovetail guide and for the first limb of the vertebra body plate to be formed complementarily in cross section. For this purpose according to one embodiment of the invention the first limb may comprise two parallel spaced runners which are connected at the ends, wherein the inner sides of the runners form the plate-side dovetail guide.

As is known per se the human vertebral column is not a straight line, but is curved double S-shaped. In order to obtain a corresponding adaptation to the anatomical circumstances one embodiment of the invention provides for the end surfaces of the end bodies, which face away from the middle body, to be inclined at an angle to the axis not equal to 90°. The inclination lies in a plane in which also the natural inclination of the vertebra bodies would run, i.e. from the outside to the inside or from the inside to the outside.

In order to obtain a further securement of the bodies against one another one embodiment of the invention provides for bores to be formed in the end surfaces of the bodies for accommodating pin-shaped securing elements. These according to a further embodiment of the invention may be formed as clips which form a latch connection with the bores. With the help of such pins the lateral position of the bodies to one another may be fixed. The pins for example are of a suitable plastic material or also titanium or of the same material as used for the end bodies and the middle body.

As mentioned the vertebra body plate is fastened with the help of one or two bone screws in the neighboring vertebra body. Furthermore the connection plate is screwed onto the same limb which accommodates the bone screws. So that attaching the connection plate may be carried out without a problem, according to a further embodiment of the invention it is provided for the head of the screw to be sunk so far into the limb that it does not protrude outwards. Preferably the head of the bone screw is formed spherically and cooperates with a spherical countersinking in the limb of the vertebra body plate so that the bone screw may be screwed into the neighboring vertebra body at a desired angle without the head protruding.

According to a further embodiment of the invention it is provided for the connection plate between the ends to comprise an elongate hole and for there to be provided an adjusting pin with thread sections on both sides of a radial collar located between the ends of the pin. With the help of the adjusting pin the distance of the connection plate to the stack of bodies may be set. With regard to the connection of the vertebra body plates to the end bodies this does not cause any problems since the angled plate is held displaceable relative to the end body.

BRIEF DESCRIPTION OF THE DRAWINGS

In the drawings wherein similar reference characters denote similar elements throughout the several views.

FIG. 8 is a lateral view of the reconstruction system according to FIG. 7 after a partial construction;

FIG. 9 is a perspectively exploded view of one embodiment of the reconstruction system;

DESCRIPTION OF THE PREFERRED EMBODIMENTS

Figure 1:
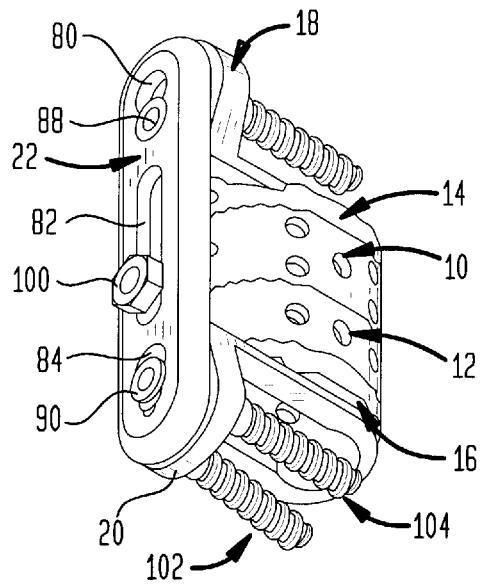
FIG. 1 is an isometric view of the reconstruction system according to the invention.
Figure 2:
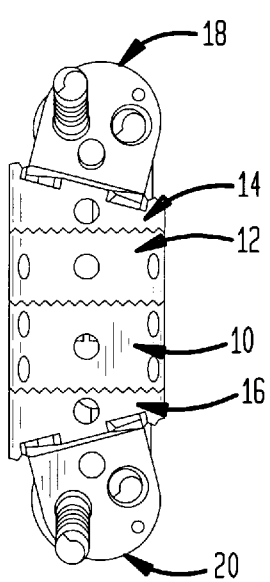
FIG. 2 is a lateral view of the system according to FIG. 1 with the connection plate removed.
Figure 3:
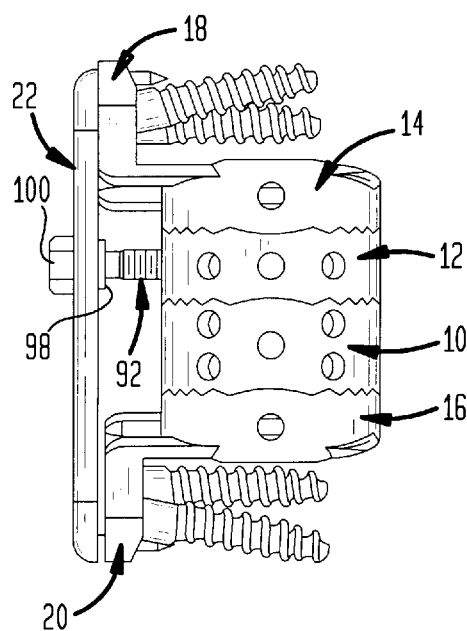
FIG. 3 is an elevation view of the system according to FIG. 1, displaced by 90°.
Figure 4:
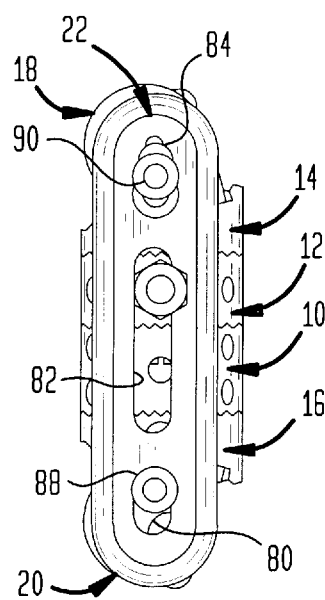
FIG. 4 is a lateral view similar to FIG. 2, however with the connection plate attached and a different inclination of the end body.
Figure 5:
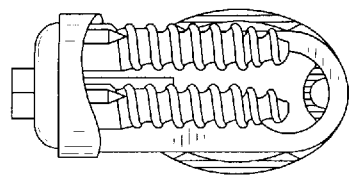
FIG. 5 is a plan view of the arrangement according to FIG. 1.
Figure 6:
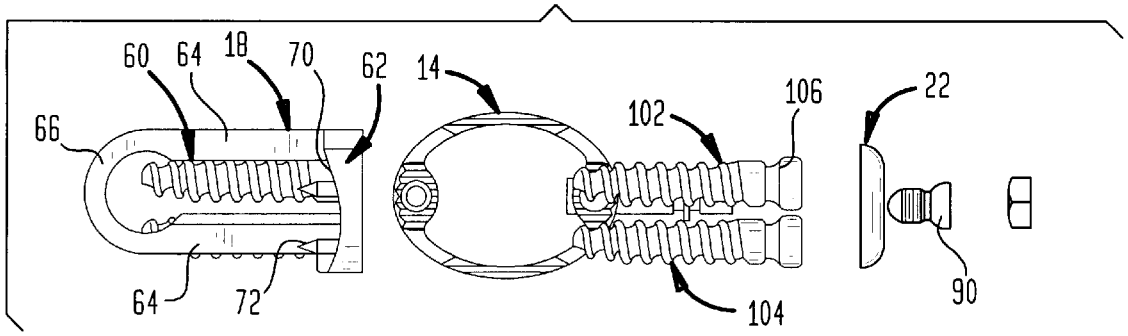
FIG. 6 is a plan view of the reconstruction system according to the invention in an exploded representation.

The reconstruction system according to the FIGS. 1 to 10 comprises middle bodies 10, 12, end bodies 14, 16, vertebra body plates 18, 20 and a connection plate 22. The bodies 10 to 16 form a stack which at the upper and lower end is limited by the vertebra body plates 18, 20, wherein the latter are connected to one another by the connection plate 22. In the following the individual parts are described in more detail.

The middle bodies 10 are annularly oval, as is best deduced from the FIGS. 6, 9, 12 and 14. As is to be recognized from FIG. 14 both end surfaces of the middle body 10 are provided with teeth 24. The apex of the teeth or the troughs or roots between the teeth run in a direction which is determined by the longer diameter 26. In the preferred embodiment the teeth extend in a direction parallel to axis 26. If several middle bodies 10 are placed over one another they can be displaced with respect to one another but however only in the direction of the teeth, whilst transversely to this they are prevented from displacing.

The middle bodies 10 furthermore comprise bores 28 at the ends of the longer axis. The bores 28 located in the thickened sections of the wall of the middle body 10. As is deduced from FIG. 13 the bore sections of the bore 28 on both sides of a radial bore comprise a shoulder 32. In FIG. 8 there is shown a securing pin 34. It consists of two hollow cylindrical sections which are separated from one another by a middle section 36. The cylindrical sections comprise axially parallel semi-circular parts separated by a slot 39. Furthermore the parts of the hollow cylindrical sections at the ends are broadened radially somewhat forming a flange The pins 32 may be clipped into the bores 28 wherein the radial flanges at the end engage behind the shoulder 32. The middle collar or section 36 comes to lie in the corresponding countersinking at the end of the bore 28. With the help of the pins 34 therefore two middle bodies arranged over one another may be secured against lateral displacement.

Figure 11:
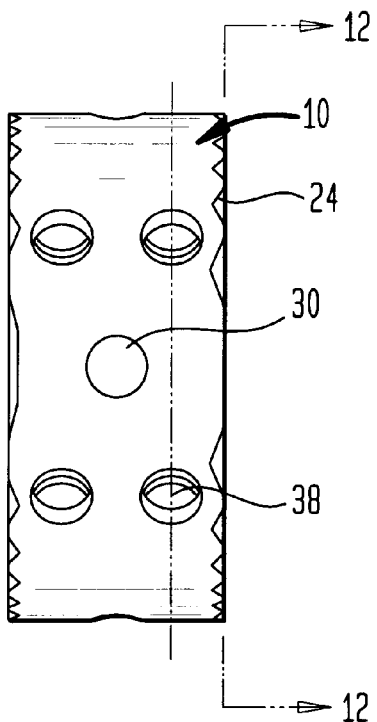
FIG. 11 is the lateral view of a middle body of the reconstruction system according to the invention.
Figure 12:
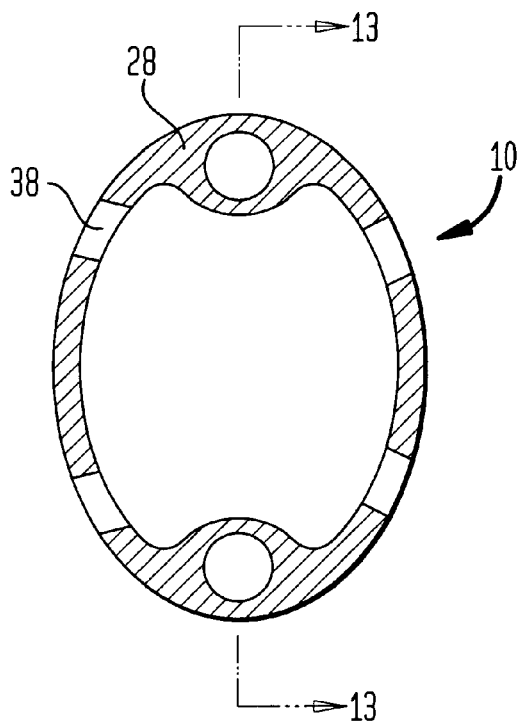
FIG. 12 is a section through the middle body according to FIG. 11 along the line 12—12.
Figure 13:
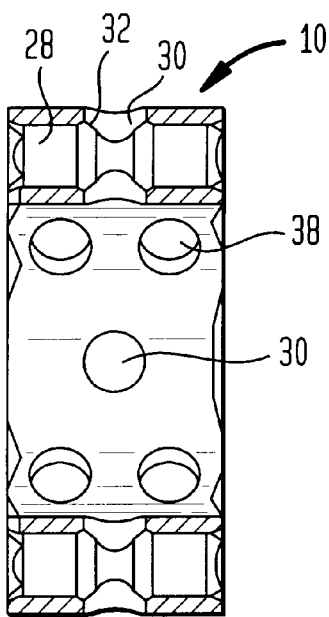
FIG. 13 is a section through the body according to FIG. 12 along line 13—13.
Figure 14:
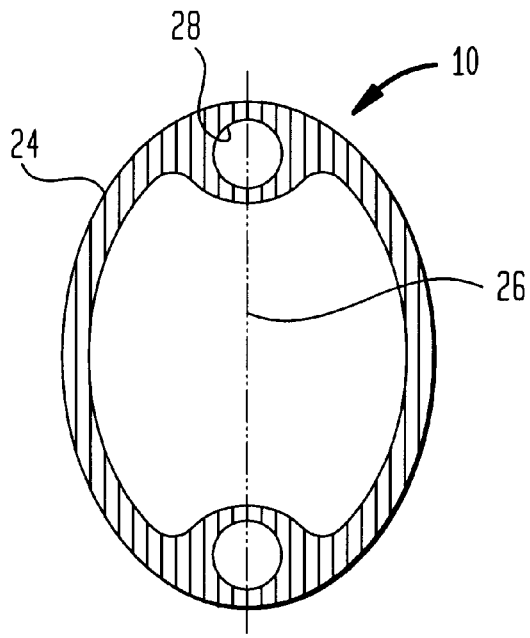
FIG. 14 is an end view of the body according to FIG. 11 in the direction of arrow 14.

Referring to FIGS. 11–13, on each side of the middle body 10 in its wall there are formed holes 38. Their axis is not perpendicular to the wall of the body 10, but at a somewhat steeper angle. The openings 38 may be provided with a thread. The same applies to the middle bore 30 which in angular circumferential spacings of 90° are arranged over half the circumference. The purpose of these bores or openings will be dealt with later.

The middle bodies 10 shown in the figures may have differing heights. Preferably one set of several middle bodies is present with graded heights. In the FIGS. 1 to 10 this is to be recognized by way of the middle body 12 which has a smaller height than the middle body 10. Body 10, however, has a particular relationship with the middle body 12, which will be discussed later.

In FIGS. 15 to 18 an end body 14 is shown in more detail. Since the end body 14 is identical to the end body 16 only one end body needs to be explained in more detail.

Figure 15:
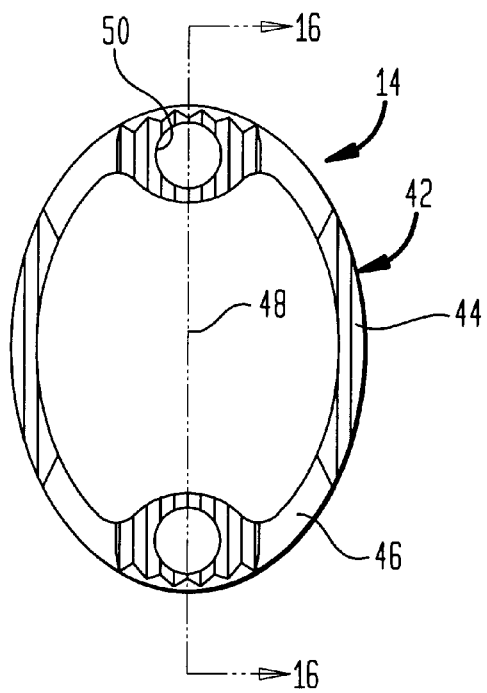
FIG. 15 is an end view of an end body of the reconstruction system according to the invention.
Figure 16:
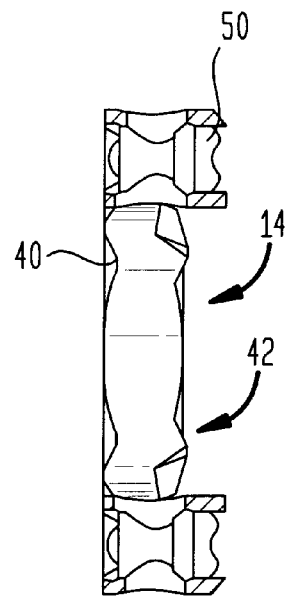
FIG. 16 is a section through the body according to FIG. 15 along line 16—16.
Figure 17:
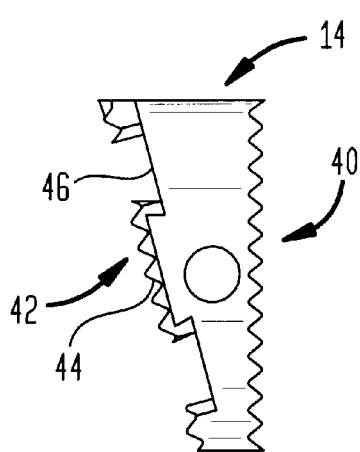
FIG. 17 is a lateral view of the end body according to FIG. 15.
Figure 18:
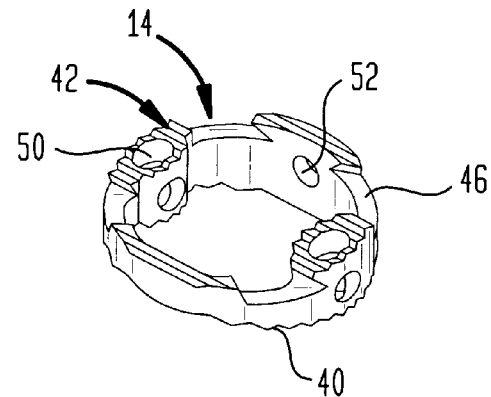
FIG. 18 is the end body according to the FIGS. 5 to 17 in a perspective view.

The end body 14 is characterized by the fact that it comprises an end surface 40 which may correspond to the end surface of a middle body 10 or is complementary to this. This means there is provided corresponding teeth which cooperate with the teeth of the middle body. The opposite lying end surface 42 comprises an inclination as shown in FIGS. 1 to 10 or also FIGS. 17 and 18. The end surface 42 is likewise provided with teeth 44 which are similar to teeth 40 or the teeth 24 of middle body 10. Teeth 44 do not serve to engage or to cooperate with the middle body, but with the neighboring vertebra body and do not fill out the whole end surface, but rather cutouts 46 are left free. These are such that they form a dovetail guide parallel to the largest diameter 48 (FIG. 15). At the ends of the largest diameter in turn there are formed bores 50 for accommodating a securing pin 34, comparable to the bores 28. At a circumferential angular spacing of 90° again there are formed radial holes 52 which may be threaded holes.

As shown in FIGS. 1 to 4, the middle bodies 10, 12 and the end bodies 14, 16 are stacked onto one another with their teeth engaging into one another. The middle and end bodies are preferably cut from a tubular blank. Therefore between neighboring bodies with an uneven cut surface there results "male" and "female" end surfaces. So that the end bodies and the middle bodies fit together independently of the position of the middle body, in the present case middle bodies are provided whose end surfaces are identical and in this manner the manufacture is simplified and the storage is reduced.

In the examples shown, the end bodies 14, 16 at the free end are provided with inclined end surfaces 42. Also annularly cylindrical end bodies may be provided with an end surface comprising a dovetail guide as was described by way of FIGS. 15 to 18. The height of these end bodies however is constant. Furthermore, the end bodies 14, 16 may be provided with different angles of inclination.

The angle plates or the vertebra body plates 18, 20 are formed identically so that a description of one plate is sufficient. As can be recognized the plates comprise two limbs 60, 62 which run at right angles to one another. The plates 18, 20 are formed as one piece. The limb 60 comprises two runners 64 running parallel at a distance which are connected to one another by a semi-circular connection section 66. The connection sections on the lower side chamfered at 68, this side lying opposite the other limb 62. The runners 64 on the edges facing one another are chamfered so that there is formed a dovetail guide 68, as for example is to be recognized in FIG. 8 or 9. The runners are inserted into the dovetail guide of the end bodies 14, 16 as is roughly to be recognized from FIGS. 1 and 3. The movement of a plate 18 away from an end body 14, 16 along the spine is therefore prevented in this manner, and specifically prevented independently of the relative position of the limb 60 in the direction of axis 26 of the end body.

The other limb 62 is plate-like and on the side facing the limb 60 is curved concavely at 70. The curved surface contains spikes 72. The limb 62 is furthermore provided with two first holes 74 and a third hole 76 of smaller diameter. The hole 76 is formed as a threaded hole.

Figure 7:
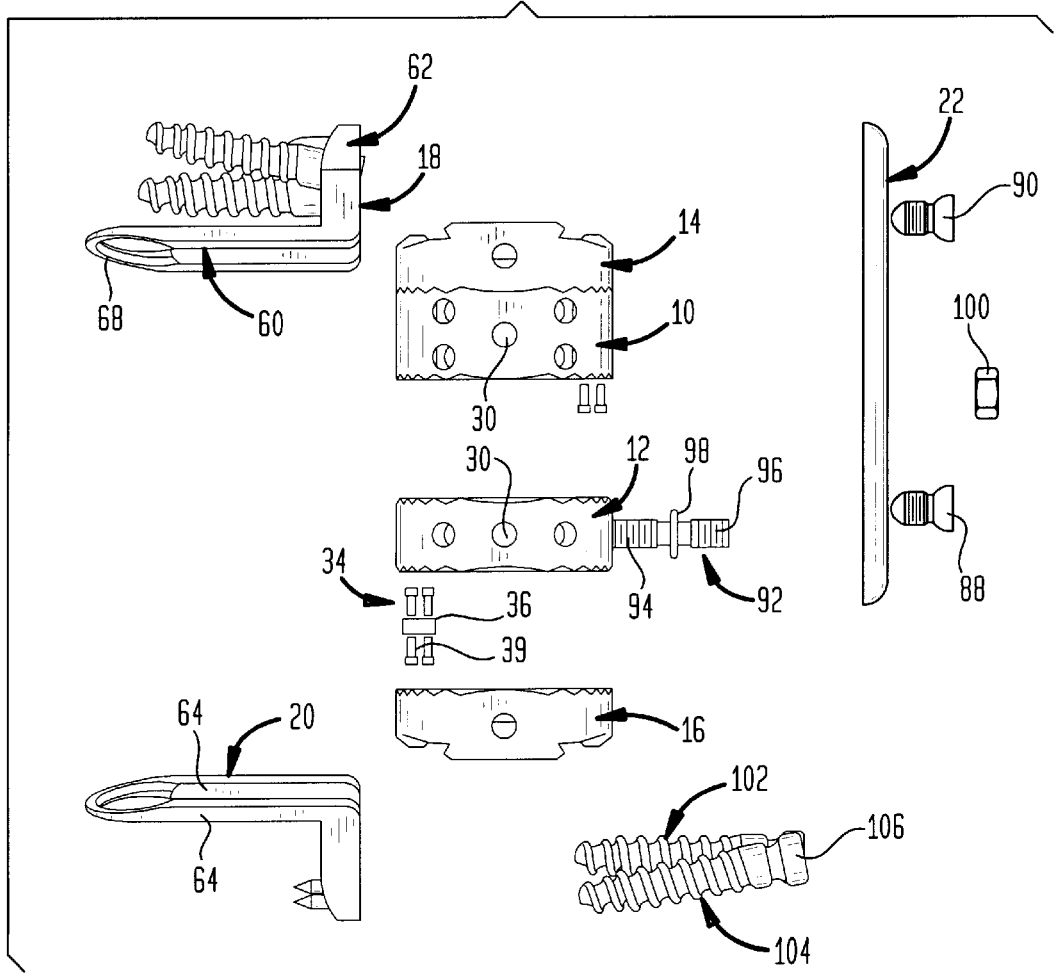
FIG. 7 is a lateral view of the reconstruction system according to FIG. 6 in an exploded representation.
Figure 10:
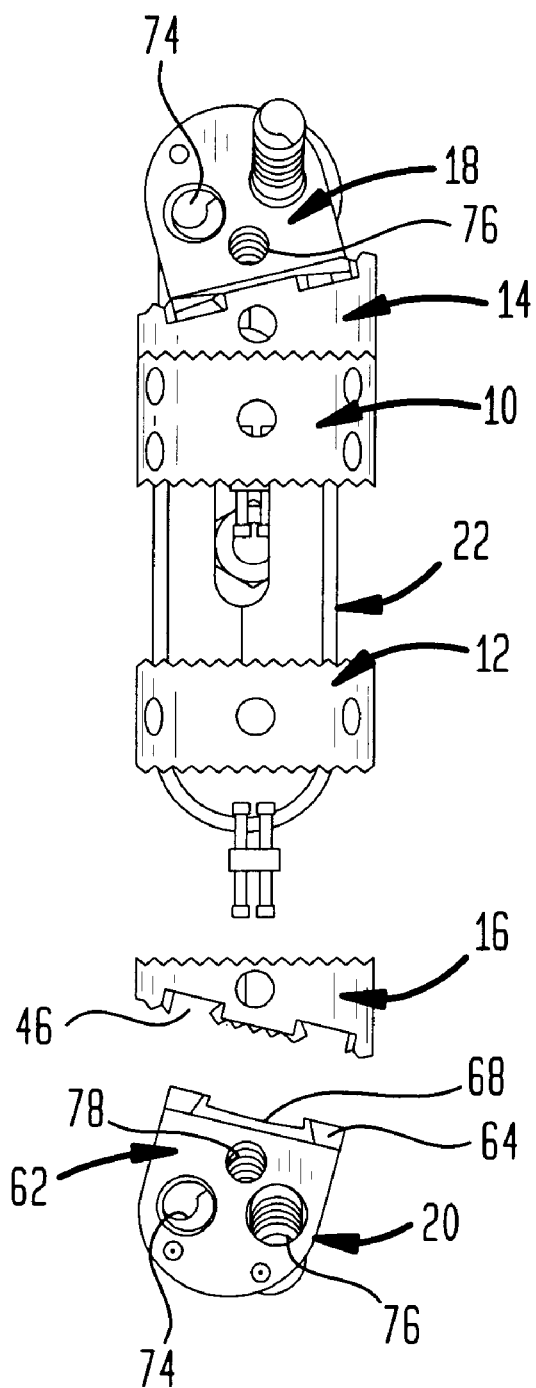
FIG. 10 is a similar representation as FIG. 2, but in an only part-constructed arrangement.

The elongate connection plate 22 is provided with three openings 80, 82 and 84. The opening 80 at one end of the plate 22 consists of two holes which are arranged next to one another but are connected for the accommodation of a screw 88 in two distanced positions. The screw 88 may with its threaded shank be screwed into the bore 78 of the plate 18 or 20. The opening 84 at the other end of the plate is elongated and narrows to the free end of the plate. Furthermore, the opening or bore 84 has a countersinking of a manner such that on screwing a screw 90 into the threaded bore 78 of the plate 18 or 20 the connection plate 22 is moved relatively, since the screw 90 displaces the plate wherein the screw gets into the wider part of the opening 84. The middle opening 82 is an elongate hole for the accommodation of an adjusting or distancing screw 92, as is shown in FIG. 7. The screw 92 comprises at two ends threaded sections 94, 96 and approximately in the middle a radial collar 98. The threaded section 94 is screwed into a middle bore 30 of a middle body which faces the connection plate 22. With this the radial collar 98 bears against the facing side of the plate 22 whilst the threaded section 98 extends through the elongated hole 82. A nut 100 is screwed onto the threaded section 96 in order to obtain a rigid connection between the screw 92 and the plate 22.

The distance between the plate 22 and the stack of the end and middle bodies is therefore determined by how far the threaded section 94 is screwed into the threaded bore 30.

The vertebra body plates 18, 20 in each case can receive two bone screws 102, 104 which comprise a threaded shank and a spherical head 106. The bone screws 102, 104 are guided through the openings 74, 76 of the limbs 62 of the plate 18, 20 and are screwed into a vertebra body (not shown), by which means the plates 18, 20 are fastened in an angularly stable manner. The spherical heads 106 are accommodated by corresponding spherical countersinkings of the holes 74, 76 so that a screwing in may be effected at any angle. Furthermore the countersinkings fully accommodate the heads 106. All parts shown in the drawings are formed from a suitable body-compatible materials, e.g. titanium.

The system shown has the object of replacing two or more vertebra bodies. The individual bodies 10, 12 or 14, 16 may also serve as a normal replacement for a vertebra disk or a vertebra body. It is also possible to connect individual end and middle bodies tacked onto one another only via connection plates of the shown type. A connection to healthy neighboring sections of the vertebral column is then to be created in the known manner.

After removing the vertebra body or bodies or also before the plates 18, 20 are fastened to the neighboring healthy vertebra bodies with the help of the bone screws 102, 104. The spikes 72 ensure an additional securement. Then a suitable stack or middle and end bodies is installed. The direction of insertion runs transversely to the axis of the vertebral column, i.e. in the direction of the largest diameter of the bodies 10 to 16. The fastening of the package or of the stack to neighboring healthy parts of the vertebral column is effected in that runners 64 of the plates 18, 20 are inserted into the corresponding dovetail guides of the end bodies 14, 16 as is roughly represented in the FIGS. 1 to 4. The securement to the side is effected in that finally the connection plate 22 with the help of the screws 90, 88 is fastened to the plates 18, 20. On account of the compression effect of the screw 90 with the hole 84 there is effected a pressing together of the body or stack so that any play is avoided. The relative position of the plates 18, 20 is adjusted by the adjusting screw or nut 100. This allows relative movement between the end bodies 14, 16 and plates 18,20 along the dovetails. This may be recognized best in FIG. 3.

In the installed position a part of the opening 38 faces in the same direction as the pedicle of the vertebra If before reconstruction a removal of the pedicle is required, threaded elements may be screwed into the openings on which then in the usual manner parts of the implant are fastened for stabilizing the vertebral column as is know per se with the application of pedicle screws.

What is claimed is:

1. A reconstruction system for vertebra, comprising:
   at least one annular middle body having end surfaces;
   two annular end bodies having end surfaces, wherein the end surfaces of the middle body and of the end bodies are formed such that the bodies may be stacked over one another and one end surface of the end bodies comprises a receiving section having an axis;
   two approximately right-angled vertebra body plates having a pair of limbs of which a first limb is formed such that in a direction perpendicular to an axis of an end body, said limb is insertable into the receiving section in a manner such that the limb is prevented from moving away from the end body in the direction of the axis, whilst a second limb includes at least one bore for a bone screw and at least one threaded bore; and
   a connection plate, having ends including openings for connection to the second limb via a screw.

2. The reconstruction system according to claim 1, wherein the bodies are oval and the axis of the receiving section runs along the larger diameter of the oval.

3. The reconstruction system according to claim 2, wherein cooperating end surfaces of the bodies have teeth such that the bodies are displaceable relative to one another only in one direction.

4. The reconstruction system according to claim 3 wherein the displacement direction runs in the direction of the large diameter of the oval.

5. The reconstruction system according to claim 1, wherein the end surfaces of the middle body are formed the same.

6. The reconstruction system according to claim 1, wherein there is provided a set of middle bodies of a graded length.

7. The reconstruction system according to claim 1, wherein the end surface of the end body, which faces the middle body, is formed complementarily to the end surfaces of the middle body.

8. The reconstruction system according to claim 1, wherein the receiving section comprises a dovetail guide and the first limb of the vertebra body plate in cross section is formed complementary thereto.

9. The reconstruction system according to claim 8, wherein the first limb comprises two parallel distanced runners which are connected at the ends.

10. The reconstruction system according to claim 9, wherein the connecting end comprises a chamfering for the simplified introduction into the receiving section.

11. The reconstruction system according to claim 10, wherein the inner sides of the runners form a dovetail guide.

12. The reconstruction system according to claim 1, wherein the end surfaces of the end bodies are inclined to the axis of the end bodies at an angle which is not equal to 90°.

13. The reconstruction system according to claim 12, wherein the angle of inclination lies in a plane which runs parallel to a plane in which the second limb of the vertebra plates lie.

14. The reconstruction system according to claim 1, wherein in the end surfaces of the bodies are oval and there are bores formed therein for the accommodation of pin-shaped securing elements.

15. The reconstruction system according to claim 14, wherein a securing element at the ends is formed as a spring clip which under the effect of the spring cooperates with the bores.

16. The reconstruction system according to claim 15, wherein the bores in the end surfaces are arranged at the ends of the oval.

17. The reconstruction system according to claim 16, wherein the head of the bone screw is countersunk in the bore of the second limb.

18. The reconstruction system according to claim 17, wherein the head of the bone screw is spherical and the opening in the second limb comprises a spherical counter-sinking.

19. The reconstruction system according to claim 18, wherein the second limb on a side proximal to the first limb comprises at least one sharp spike.

20. The reconstruction system according to claim 1, wherein the connection plate between the ends comprises an elongate hole and there is provided an adjusting pin with threaded sections formed on both sides of a radial collar located between ends of the pin, a first threaded section for setting the distance of the connection plate to the bodies and the other threaded section extends through the elongate hole and is connected to the plate with a nut.

* * * * *